(12) United States Patent
Walz et al.

(10) Patent No.: US 6,969,777 B2
(45) Date of Patent: Nov. 29, 2005

(54) METHOD FOR THE HYDROFORMYLATION OF OLEFINS COMPRISING 2 TO 8 CARBON ATOMS

(75) Inventors: Helmut Walz, Ludwigshafen (DE); Willi Schönmann, Limburgerhof (DE); Rolf Müller, Dannstadt-Schauernheim (DE); Roland Krokoszinski, Weisenheim a.Berg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 144 days.

(21) Appl. No.: 10/312,360

(22) PCT Filed: Jun. 27, 2001

(86) PCT No.: PCT/EP01/07342

§ 371 (c)(1),
(2), (4) Date: Dec. 26, 2002

(87) PCT Pub. No.: WO02/00583

PCT Pub. Date: Jan. 3, 2002

(65) Prior Publication Data

US 2003/0176743 A1 Sep. 18, 2003

(30) Foreign Application Priority Data

Jun. 28, 2000 (DE) .......................................... 100 31 519

(51) Int. Cl.⁷ ............................................. C07C 45/50
(52) U.S. Cl. ....................... 568/451; 568/454
(58) Field of Search .................................. 568/451, 454

(56) References Cited

U.S. PATENT DOCUMENTS

| 4,778,929 A | 10/1988 | Zehner et al. .............. 568/454 |
| 6,100,432 A | 8/2000 | Borget et al. ............... 568/454 |
| 2003/0153791 A1 | 8/2003 | Richter et al. |
| 2004/0015011 A1 | 1/2004 | Krokoszinski et al. |
| 2004/0024259 A1 | 2/2004 | Richter et al. |

FOREIGN PATENT DOCUMENTS

| EP | 158 196 | 10/1985 |
| EP | 648 730 | 4/1995 |
| GB | 2 055 367 | 3/1981 |

*Primary Examiner*—Johann Richter
*Assistant Examiner*—Sikarl A. Witherspoon
(74) *Attorney, Agent, or Firm*—Keil & Weinkauf

(57) ABSTRACT

Olefins having from 2 to 8 carbon atoms are hydroformylated in a process in which (i) an olefin-containing feed in which a proportion of a saturated hydrocarbon having from 2 to 8 carbon atoms is present and also carbon monoxide and hydrogen are fed into a reaction zone and reacted in the presence of a hydroformylation catalyst, (ii) a stream consisting essentially of unreacted olefin and saturated hydrocarbon is separated off from the output from the reaction zone, (iii) the stream is separated into an olefin-enriched fraction and an olefin-depleted fraction by rectification, and (iv) at least part of the olefin-enriched fraction is recirculated to the reaction zone.

9 Claims, 1 Drawing Sheet

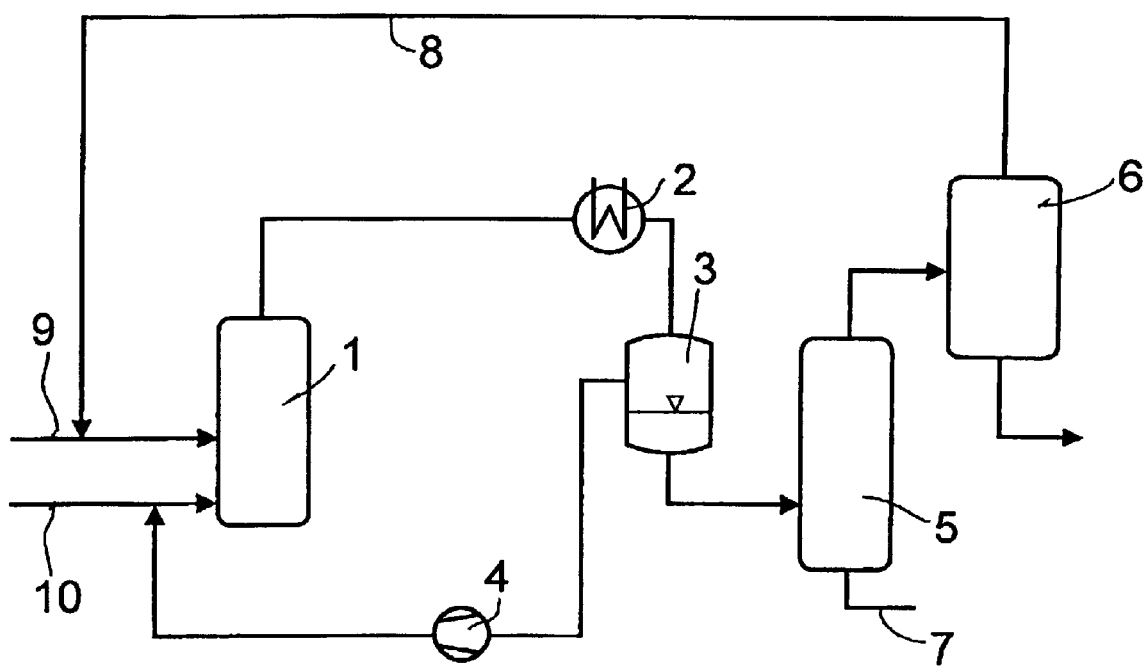

METHOD FOR THE HYDROFORMYLATION OF OLEFINS COMPRISING 2 TO 8 CARBON ATOMS

The present invention relates to a process for the hydroformylation of olefins having from 2 to 8 carbon atoms.

Hydroformylation or the oxo process is an important industrial process for preparing aldehydes from olefins, carbon monoxide and hydrogen. These aldehydes can, if desired, be hydrogenated by means of hydrogen in the same process step or subsequently in a separate hydrogenation step to give the corresponding alcohols. The hydroformylation is carried out in the presence of catalysts which are homogeneously dissolved in the reaction medium. Catalysts used are generally compounds or complexes of metals of transition group VIII, especially Co, Rh, Ir, Pd, Pt or Ru compounds or complexes, which may be unmodified or modified with, for example, amine- or phosphine-containing compounds.

Since a quantitative conversion of the olefin in hydroformylation requires a high outlay in terms of apparatus, the hydroformylation of lower olefins in particular is usually carried out only to a partial conversion. The hydroformylation product is separated from the output from the reaction and the unreacted olefin is then recirculated to the hydroformylation reactor together with fresh carbon monoxide and hydrogen. However, inert components, e.g. saturated hydrocarbons, which are not accessible to the hydroformylation reaction and have been introduced with the olefin or formed by secondary reactions, are returned to the reactor with the recirculated olefin. To prevent the concentration of inert components continually increasing in the hydroformylation reactor and reaching values at which the hydroformylation reaction ceases, a substream of the recirculated stream continuously has to be discharged from the process in order to remove the inert components from the system.

However, this bleed stream consists only partly of inert components. The major part is made up of unreacted olefin and unreacted carbon monoxide and hydrogen, which are thus lost from the reaction. To keep the bleed stream small and keep the losses associated therewith low, an olefin feed of high purity is generally used. Thus, in the hydroformylation of propylene, use is generally made of a propylene feed having a purity of about 99.5% with the balance being essentially propane. This is sometimes known as "polymer grade propylene". However, such high-purity olefin feeds are costly to obtain and therefore command significantly higher market prices than do olefins of lower purity. Thus, for example, "chemical grade propylene" which contains from about 3 to 7% by weight of propane is considerably cheaper than the abovementioned polymer grade propylene.

For the reasons mentioned, olefin feeds of lower purity, which contain, for example, more than 0.5% by weight of saturated hydrocarbons, cannot be used in industrial hydroformylation processes without specific measures being taken. To prevent the concentration of saturated hydrocarbons in the hydroformylation reactor reaching values which are so high that the hydroformylation ceases, the bleed stream would have to be so large that the associated loss of unreacted olefin would wipe out the savings achieved by using the cheaper feedstock.

EP-A 0 648 730 discloses a process for preparing an oxo product obtained from propylene, in which a gas stream comprising unreacted propylene and propane is separated off from the product stream from a propylene hydroformylation. Selective adsorption of propylene on an adsorbent and subsequent desorption give a propylene-enriched gas stream which is at least partly recirculated to the reaction zone. The alternating adsorption and desorption cycles require periodic pressure and/or temperature changes. The apparatuses required for this are complicated and susceptible to malfunctions.

It is an object of the present invention to provide an improved process for the hydroformylation of olefins which allows the use of olefin-containing feeds in which a proportion of saturated hydrocarbons is present.

We have found that this object is achieved by a process for the hydroformylation of olefins having from 2 to 8 carbon atoms, in which (i) an olefin-containing feed in which a proportion of a saturated hydrocarbon having from 2 to 8 carbon atoms is present and carbon monoxide and hydrogen are fed into a reaction zone and reacted in the presence of a hydroformylation catalyst,
(ii) a stream consisting essentially of unreacted olefin and saturated hydrocarbon is separated off from the output from the reaction zone,
(iii) the stream is separated into an olefin-enriched fraction and an olefin-depleted fraction by rectification, and
(iv) at least part of the olefin-enriched fraction is recirculated to the reaction zone.

Olefins which can be hydroformylated by the process of the present invention contain from 2 to 8, preferably from 2 to 4, carbon atoms. They can be straight-chain, branched or cyclic olefins. Preferred examples of suitable olefins are ethene, propene, 1-butene and/or 2-butene. The olefin-containing feed can comprise a single olefin or a mixture of olefins. The olefin is fed into the reaction zone in the form of an olefin-containing feed containing, for example, from 0.5 to 40% by weight, preferably from 2 to 30% by weight, in particular from 3 to 10% by weight, of at least one saturated hydrocarbon, i.e. an alkane and/or cycloalkane, having from 2 to 8 carbon atoms. In general, the olefin and the saturated hydrocarbon have the same number of carbon atoms. The olefin-containing feed usually consists essentially of only olefin and saturated hydrocarbon, i.e. it preferably contains less than 0.5% by weight of components other than olefin and saturated hydrocarbon.

Suitable olefin-containing feeds are available on an industrial scale. A preferred example is a mixture of propane and propene, preferably containing from 2 to 10% by weight, in particular from 3 to 7% by weight, of propane. Such mixtures are commercially available as "chemical grade propylene". They are obtained, for example, by conversion of naphtha or natural gas in steam crackers and subsequent work-up by distillation. A further example of a suitable olefin-containing feed is "refinery grade propylene" which has propane contents of from 20 to 40% by weight.

Carbon monoxide and hydrogen are usually used in the form of a mixture, known as synthesis gas. The composition of the synthesis gas used in the process of the present invention can vary within a wide range. The molar ratio of carbon monoxide to hydrogen is generally from 2:1 to 1:2, in particular from about 45:55 to 50:50.

The temperature in the hydroformylation reaction is generally in a range from about 50 to 200° C., preferably from about 60 to 190° C., in particular from about 90 to 190° C. The reaction is preferably carried out at a pressure in the range from about 10 to 700 bar, preferably from 15 to 200 bar, in particular from 15 to 60 bar. The reaction pressure can be varied as a function of the activity of the hydroformylation catalyst used.

Suitable pressure-rated reaction apparatuses for hydroformylation are known to those skilled in the art. They include the generally customary reactors for gas-liquid reactions, e.g. gas circulation reactors, bubble columns, etc., which may optionally be divided by internals.

Suitable hydroformylation catalysts are the customary transition metal compounds and complexes known to those skilled in the art, which can be used either with or without cocatalysts. The transition metal is preferably a metal of transition group VIII of the Periodic Table, in particular Co, Ru, Rh, Pd, Pt, Os or Ir, especially Rh, Co, Ir or Ru.

Suitable complexes are, for example, the carbonyl compounds of the abovementioned metals and also complexes whose ligands are selected from among amines, arylphosphines, alkylphosphines, arylalkylphosphines, olefines, dienes, etc., and mixtures thereof.

Examples of suitable catalysts are rhodium complexes of the formula $RhX_m L^1 L^2 (L^3)_n$, where X is halide, preferably chloride or bromide, alkylcarboxylate or arylcarboxylate, acetylacetonate, arylsulfonate or alkylsulfonate, in particular phenylsulfonate and toluenesulfonate, hydride or the diphenyltriazine anion, $L^1$, $L^2$, $L^3$ are, independently of one another, CO, olefins, cycloolefins, preferably cyclooctadiene (COD), dibenzophosphole, benzonitrile, $PR_3$ or $R_2P$-A-$PR_2$, and m is 1 or 3 and n is 0, 1 or 2. Radicals R (which may be identical or different) are alkyl, cycloalkyl and aryl radicals, preferably phenyl, p-tolyl, m-tolyl, p-ethylphenyl, p-cumyl, p-t-butylphenyl, p-$C_1$–$C_4$-alkoxyphenyl, preferably p-anisyl, xylyl, mesityl, p-hydroxyphenyl, which may also be ethoxylated, sulfophenyl, isopropyl, $C_1$–$C_4$-alkoxy, cyclopentyl or cyclohexyl. A is 1,2-ethylene or 1,3-propylene. $L^1$, $L^2$ and $L^3$ are each preferably, independently of one another, CO, COD, P(phenyl)$_3$, P(i-propyl)$_3$, P(anisyl)$_3$, P(OC$_2$H$_5$)$_3$, P(cyclohexyl)$_3$, dibenzophosphole or benzonitrile.

X is preferably hydride, chloride, bromide, acetate, tosylate, acetylacetonate or the diphenyltriazine anion, in particular hydride, chloride or acetate.

Preferred hydroformylation catalysts are phosphorus-containing rhodium catalysts as are formed, for example, in situ under hydroformylation conditions from a rhodium source and a triarylphosphine such as triphenylphosphine, for example $RhH(CO)_2(PPh_3)_2$ or $RhH(CO)(PPh_3)_3$.

Suitable hydroformylation catalysts are described, for example, in Beller et al., Journal of Molecular Catalysis A, 104 (1995), pp. 17–85, which is hereby fully incorporated by reference.

A partial conversion, based on the olefin fed in, takes place per pass through the reaction zone. The conversion is generally from 10 to 90%, based on the olefin fed in.

The output from the reaction zone is subjected to a single-stage or multistage separation operation to give at least a stream comprising the major part of the hydroformylation product and a stream consisting essentially of unreacted olefin and saturated hydrocarbon. Depending on the output method, further streams, e.g. waste gases comprising synthesis gas and streams comprising high-boiling by-products of the hydroformylation and/or hydroformylation catalyst, may be obtained and are, if appropriate after work-up, wholly or partly recirculated to the reaction zone or discharged from the process. For example, the hydroformylation product and any components having higher boiling points than the hydroformylation product can firstly be separated off from the output from the reaction zone. Subsequently, a mixture of unreacted olefin and saturated hydrocarbon can be condensed out.

However, the stream consisting essentially of unreacted olefin and saturated hydrocarbon is advantageously obtained by firstly separating off a crude hydroformylation product comprising unreacted olefin and saturated hydrocarbon in dissolved form from the output from the reaction zone and then subjecting the crude liquid hydroformylation product to a degassing step, giving a stream which consists essentially of unreacted olefin and saturated hydrocarbon. The remainder of the reaction mixture from which the crude hydroformylation product has been separated is generally wholly or partly recirculated to the reaction zone. The crude hydroformylation product can be degassed by depressurizing it, heating it and/or treating it with a stripping gas such as synthesis gas or nitrogen. The degassing is advantageously carried out in a column where the crude hydroformylation product is fed in in the region of the middle of the column, the degassed hydroformylation product is taken off at the bottom of the column and passed to further work-up, and a liquid or gaseous stream consisting essentially of unreacted olefin and saturated hydrocarbon is taken off the top of the column.

The separation of the crude hydroformylation product from the output from the reaction zone can be carried out in various ways. One way is to use the liquid output process, in which the essentially—apart from the synthesis gas used in excess for the hydroformylation—liquid output from the reaction zone is depressurized so that it is, as a result of the pressure reduction, separated into a liquid phase which consists essentially of high-boiling by-products, the homogeneously dissolved hydroformylation catalyst and small amounts of hydroformylation product, unreacted olefin and saturated hydrocarbon, and a gas phase which consists essentially of hydroformylation product, unreacted olefin and saturated hydrocarbon together with unreacted synthesis gas. The liquid phase can be recirculated to the reactor as recycle stream. The crude hydroformylation product is obtained by at least partial condensation of the gas phase. The gas phase remaining after the condensation is wholly or partly recirculated to the reaction zone.

The gas and liquid phase obtained initially in the depressurization step can advantageously be worked up by the process described in WO 97/07086. For this purpose, the liquid phase is heated and introduced into the upper region of a column, while the gas phase is introduced into the bottom of the column. Liquid phase and gas phase are thus conveyed in countercurrent. To increase mutual contact of the phases, the column is preferably provided with packing. As a result of the intimate contact of the gas phase with the liquid phase, the residual amounts of hydroformylation product, unreacted olefin and saturated hydrocarbon present in the liquid phase are transferred to the gas phase, so that the gas stream leaving the top of the column is enriched in hydroformylation product, unreacted olefin and saturated hydrocarbon compared to the gas stream introduced at the lower end of the column. The further work-up of the gas stream leaving the column and of the liquid phase leaving the column is carried out in a customary manner, for example as described above.

Alternatively, it is possible to employ, particularly with the use of $C_2$–$C_4$-olefins, the gas recycle process, in which a gas stream is taken off from the gas space of the hydroformylation reactor. This gas stream consists essentially of synthesis gas, unreacted olefin and saturated hydrocarbon together with an amount, determined by the vapor pressure in the hydroformylation reactor, of the hydroformylation product formed in the hydroformylation reaction. The hydroformylation product present in the gas stream is separated off from the gas stream, e.g. condensed out by cooling, and the gas stream which has been freed of the liquid component is recirculated to the hydroformylation reactor.

The stream consisting essentially of unreacted olefin and saturated hydrocarbon comprises, for example, from 50 to 95% by weight, preferably from 60 to 80% by weight, of olefin and from 5 to 50% by weight, preferably from 20 to 40% by weight, of saturated hydrocarbon.

The stream consisting essentially of unreacted olefin and saturated hydrocarbon is separated into an olefin-enriched fraction and an olefin-depleted fraction by rectification (distillation). The rectification is usually carried out at low temperature and/or superatmospheric pressure, with the precise temperature and/or pressure conditions depending on factors such as the number of carbon atoms in the olefin/saturated hydrocarbon to be separated, etc. The rectification is generally carried out in a column which is provided with a sufficiently large number of rectification trays. Columns for such separation tasks are known per se and are used, for example, for the separation of olefins and saturated hydrocarbons present in the cracker gas from a steam cracker. The stream to be fractionated can be introduced into the column either in gaseous form or in liquid form, preferably in the region of the middle of the column. The olefin-enriched fraction can advantageously be taken off at the top or in the upper region of the column, and the olefin-depleted fraction can advantageously be taken off at the bottom or in the lower region of the column.

In general, efforts are made to obtain an olefin-depleted fraction consisting of substantially pure saturated hydrocarbon, so that it can be discharged from the process without resulting in a relatively large loss of olefin. In contrast, pure olefin is generally not sought in the case of the olefin-enriched fraction, but instead a certain content of saturated hydrocarbons is permitted so as to reduce the cost of the separation. For the purposes of the present invention, it is sufficient for the olefin-enriched fraction to be enriched in olefin compared to the output from the reaction zone, i.e. the ratio of olefin to saturated hydrocarbon in it is greater than in the output from the reaction zone.

The olefin-depleted fraction preferably comprises more than 95% by weight, in particular more than 99% by weight, of saturated hydrocarbon. The olefin-enriched fraction usually comprises more than 80% by weight, e.g. from 85 to 95% by weight, of olefin, with the balance being saturated hydrocarbon.

In a particularly preferred embodiment of the process of the present invention, a propylene-containing feed in which a proportion of propane is present is used. A mixture of propylene and propane is therefore obtained as stream to be separated. The separation of this stream into a propylene-enriched fraction and a propylene-depleted fraction is carried out in a suitable distillation column operated under superatmospheric pressure, namely a $C_3$ splitter. The column is preferably operated so that a propylene-enriched fraction which can be recirculated directly to the reaction zone is obtained at the top, and largely pure propane which can be removed from the system without loss of propylene can be taken off at the bottom. Typical operating conditions for the $C_3$ splitter are: pressure at the top=20 to 25 bar, temperature at the bottom=60 to 70° C., from 100 to 150 theoretical plates.

The olefin-depleted fraction is discharged from the system. It can, for example, be burnt. It can also be used as feedstock for chemical reactions, e.g. in a steam cracker. In a particularly advantageous embodiment, the olefin-depleted fraction is fed to a steam cracker from whose cracker gas the olefin-containing feed for the process of the present invention is obtained. After attainment of steady-state operation of the process of the present invention, an amount of saturated hydrocarbon which corresponds essentially to the sum of the amount of saturated hydrocarbon introduced with the olefin-containing feed and the amount formed in the hydroformylation is discharged together with the olefin-depleted fraction.

The process of the present invention starts from olefin-containing feeds in which a proportion of a saturated hydrocarbon is present. Such mixtures are obtained on an industrial scale and isolation of them is considerably less costly than that of the corresponding highly purified olefin feeds. Although a point downstream of the hydroformylation is required for separation of olefin and saturated hydrocarbon in the process of the invention, the fractionation of an olefin/saturated hydrocarbon stream separated from the hydroformylation product is significantly simpler and less costly than the fractionation of the entire olefin-containing feed, since the stream obtained after the hydroformylation is reduced by the proportion of olefin which has been converted into aldehyde and/or alcohol in the hydroformylation reaction. The amounts of mixture to be fractionated are considerably lower in the stage downstream of the reaction zone than in the entire feed. Thus, the separation plant can be made smaller, which is associated with lower capital costs. A further advantage is that the olefin content of the olefin-enriched fraction has to be increased only to a sufficient extent for the weight ratio of olefin to saturated hydrocarbon in the olefin-enriched fraction to be greater than that in the output from the reaction zone. An olefin-containing feed in conventional hydroformylation processes generally has significantly higher olefin contents, e.g. about 99.5%.

An advantageous embodiment of the process of the present invention is shown in FIG. 1 and is explained below.

FIG. 1 shows a schematic flow diagram of the process of the present invention carried out by the gas recycle method. Self-evident plant details which are not necessary to illustrate the process of the present invention have been omitted in the interests of clarity.

In FIG. 1, an olefin-containing feed (9) comprising the olefin to be hydroformylated and a saturated hydrocarbon, and an olefin-containing stream recirculated via line (8) together with synthesis gas (10), i.e. a mixture of carbon monoxide and hydrogen, are fed into the reactor (1) and hydroformylated there to partial conversion. A gaseous stream comprising unreacted olefin, saturated hydrocarbon, unreacted synthesis gas and a hydroformylation product is taken from the gas space of the reactor. The stream is cooled in the heat exchanger (2) and passed to a phase separation vessel (3). The gaseous part is recirculated via the compressor (4) to the reactor (1). The liquid obtained in the separation vessel (3), which consists essentially of crude hydroformylation product together with olefin and saturated hydrocarbon dissolved therein, is fed to the degassing column (5) at the top of which a mixture of olefin and saturated hydrocarbon is obtained. At the bottom of the degassing column (5), the crude hydroformylation product (7) is taken off and is subsequently processed further. The mixture of olefin and saturated hydrocarbon is fed to the rectification column (6). There, an olefin stream having a reduced proportion of saturated hydrocarbon is obtained at the top and is recirculated via line (8) to the hydroformylation reactor (1). At the bottom of the rectification column (6), an essentially pure saturated hydrocarbon is obtained and is removed from the system.

The invention is illustrated by the following example.

EXAMPLE

A plant as shown in FIG. 1 is used.

A feed stream of 10 t/h of chemical grade propylene (95% propylene, 5% propane), a recycle stream (8) of 3.2 t/h from the propylene/propane separation column (6) and synthesis gas were fed to the reactor (1). A liquid phase comprising high boilers and an Rh/triphenylphosphine catalyst homogeneously dissolved therein was present in the reactor. The hydroformylation was carried out at 105° C. and 20 bar. The product formed, namely a mixture of n-butyraldehyde and isobutyraldehyde, was discharged from the reactor, together with unreacted propylene and the propane introduced and formed, by means of a circulating gas stream. The condensable components were condensed in the downstream cooler (2) and collected in the subsequent separator (3). The condensate contained 78.3% of butyraldehyde, 14.3% of propylene and 7.4% of propane. It was fed (20.3 t/h) to the degassing column (5) where a $C_3$-free hydroformylation product (15.9 t/h) was obtained at the bottom and a mixture of 66% of propylene and 34% of propane (4.4 t/h) was obtained at the top. The latter mixture was fractionated in the subsequent column (6) to give a virtually propylene-free propane stream at the bottom (1.2 t/h) and a mixture of 90% of propylene and 10% of propane at the top (3.2 t/h). The latter stream was recirculated to the propylene feed to the synthesis reactor (1). The column (6) was operated at a pressure at the top of from 20 to 21 bar and a temperature at the bottom of from 60 to 70° C. and had 130 theoretical plates.

We claim:

1. A process for the hydroformylation of olefins having from 2 to 8 carbon atoms, in which
   (i) an olefin-containing feed in which a proportion of a saturated hydrocarbon having from 2 to 8 carbon atoms is present and also carbon monoxide and hydrogen are fed into a reaction zone and reacted in the presence of a hydroformylation catalyst,
   (ii) a stream consisting essentially of unreacted olefin and saturated hydrocarbon is separated off from the output from the reaction zone,
   (iii) the stream is separated into an olefin-enriched fraction and an olefin-depleted fraction by rectification, and
   (iv) at least part of the olefin-enriched fraction is recirculated to the reaction zone.

2. A process for the hydroformylation of olefins having from 2 to 8 carbon atoms, in which
   (i) an olefin-containing feed in which a proportion of a satu- rated hydrocarbon having from 2 to 8 carbon atoms is present and also carbon monoxide and hydrogen are fed into a reac- tion zone and reacted in the presence of a hydroformylation catalyst.
   (ii) a stream consisting essentially of unreacted olefin and sat- urated hydrocarbon is separated off from the reaction zone.
   (iii) the stream is separated into an olefin-enriched fraction and an olefin-depleted fraction by rectification, and
   (iv) at least part of the olefin-enriched fraction is recirculated to the reaction zone, and in which the stream consisting essentially of unreacted ole- fin and saturated hydrocarbon is obtained by firstly separating off a crude hydroformylation product comprising unreacted olefin and saturated hydrocarbon in dissolved form from the output from the reaction zone and subjecting the crude hydroformylation prod- uct to a degassing step.

3. A process as claimed in claim 2, in which the output from the reaction zone is essentially gaseous and the crude hydroformylation product is separated off by condensation from the gaseous output.

4. A process as claimed in claim 2, in which the output from the reaction zone is essentially liquid, the liquid output is depressurized so that it is separated into a liquid phase which consists essentially of high-boiling by-products, the homogeneously dissolved hydroformylation catalyst and small amounts of hydroformylation product, small amounts of unreacted olefin and small amounts of saturated hydrocarbon, and a gas phase which consists essentially of hydroformylation product, unreacted olefin and saturated hydrocarbon and also unreacted carbon monoxide and hydrogen, and the crude hydroformylation product is obtained by at least partial condensation of the gas phase.

5. A process as claimed in claim 1, in which the hydroformylation catalyst used is a phosphorus-containing rhodium catalyst.

6. A process as claimed in claim 1, in which the olefin and the saturated hydrocarbon have the same number of carbon atoms.

7. A process as claimed in claim 6, in which the olefin-containing feed is a mixture of propane and propylene.

8. A process as claimed in claim 7, in which the mixture contains from 2 to 10% by weight of propane.

9. A process as claimed in claim 1, in which the olefin-depleted fraction is fed to a steam cracker.

\* \* \* \* \*

UNITED STATES PATENT AND TRADEMARK OFFICE
CERTIFICATE OF CORRECTION

PATENT NO. : 6,969,777 B2
APPLICATION NO. : 10/312360
DATED : November 28, 2005
INVENTOR(S) : Walz et al.

It is certified that error appears in the above-identified patent and that said Letters Patent is hereby corrected as shown below:

Claim 2: Column 7, line 51, "hydrofor mylation" should read --hydroformylation--

Claim 2: Column 8, line 2, "satu- rated" should read --saturated--

Claim 2: Column 8, line 4, "reac- tion" should read --reaction--

Claim 2: Column 8, line 5, a comma should be inserted after "catalyst"

Claim 2: Column 8, line 7, "satu- rated" should read --saturated--

Claim 2: Column 8, line 14, "ole- fin" should read --olefin--

Claim 2: Column 8, line 19, "prod- uct" should read --product--

Signed and Sealed this

Third Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 6,969,777 B2  
APPLICATION NO. : 10/312360  
DATED : November 29, 2005  
INVENTOR(S) : Walz et al.

Page 1 of 1

It is certified that error appears in the above-identified patent and that said Letters Patent is hereby corrected as shown below:

Claim 2: Column 7, line 51, "hydrofor mylation" should read --hydroformylation--

Claim 2: Column 8, line 2, "satu- rated" should read --saturated--

Claim 2: Column 8, line 4, "reac- tion" should read --reaction--

Claim 2: Column 8, line 5, a comma should be inserted after "catalyst"

Claim 2: Column 8, line 7, "satu- rated" should read --saturated--

Claim 2: Column 8, line 14, "ole- fin" should read --olefin--

Claim 2: Column 8, line 19, "prod- uct" should read --product--

This certificate supersedes Certificate of Correction issued April 3, 2007.

Signed and Sealed this

Eighth Day of May, 2007

JON W. DUDAS  
*Director of the United States Patent and Trademark Office*

UNITED STATES PATENT AND TRADEMARK OFFICE
CERTIFICATE OF CORRECTION

PATENT NO. : 6,969,777 B2  Page 1 of 1
APPLICATION NO. : 10/312360
DATED : November 29, 2005
INVENTOR(S) : Walz et al.

It is certified that error appears in the above-identified patent and that said Letters Patent is hereby corrected as shown below:

In Claim 2, col. 8, line 8:
"is separated off from the" should read --is separated off from the output from the--

Signed and Sealed this

Twenty-first Day of August, 2007

JON W. DUDAS
*Director of the United States Patent and Trademark Office*